US006756592B1

(12) United States Patent
Smith et al.

(10) Patent No.: US 6,756,592 B1
(45) Date of Patent: Jun. 29, 2004

(54) APPARATUS FOR GAS FILTER CORRELATION RADIOMETRY AND METHODS FOR 2-DIMENSIONAL AND 3-DIMENSIONAL ATMOSPHERIC SOUNDING

(75) Inventors: Mark William Smith, Albuquerque, NM (US); Boris Vyacheslavovich Khattatov, Boulder, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 140 days.

(21) Appl. No.: 09/920,235

(22) Filed: Aug. 1, 2001

Related U.S. Application Data

(60) Provisional application No. 60/255,225, filed on Dec. 12, 2000, and provisional application No. 60/257,675, filed on Dec. 20, 2000.

(51) Int. Cl.[7] .............................................. G01N 21/35
(52) U.S. Cl. .................................................. 250/338.5
(58) Field of Search ...................................... 250/338.5

(56) References Cited

U.S. PATENT DOCUMENTS

| 4,543,481 A | * | 9/1985 | Zwick .................... 250/339.03 |
| 4,641,973 A | | 2/1987 | Nestler et al. |
| 4,780,613 A | | 10/1988 | Berstein et al. |
| 5,656,813 A | * | 8/1997 | Moore et al. ................ 250/330 |

FOREIGN PATENT DOCUMENTS

EP          0241522 B1 *  2/1997  .......... G01N/21/35

OTHER PUBLICATIONS

James Sandsten et al., "Real–time gas–correlation imaging employing thermal background radiation." Optics Express, vol. 6, No. 4 (Feb. 14, 2000) pp. 92–103.*

Reichle, Henry G., Connors, Vickie S., Holland, Alvin, Hypes, Warren D., and Wallio, Andrew, Middle and Upper Tropospheric Carbon Monoxide Mixing Ratios as Measured by a Satellite–Borne Remote Sensor During Nov. 1981, Journal of Geophysical Research, vol. 91, No. D10, pp. 10,865–10,887, Sep. 20, 1986.

Drummond, J.R., Measurements of Pollution in the Tropospher (MOPITT), The Use of EOS for Studies of Atmospheric Physics, pp. 77–101 (1992).

Warner, Juying X., Gille, John C., Edwards, David P., Ziskin, Dan C., Smith, Mark W., Bailey, Paul L., and Rokke, Laurie, "Cloud detection and clearing for the Earth Observing System Terra satellite Measurements of Pollution in the Troposphere (MOPITT) experiment," Applied Optics, vol. 40, No. 8, Mar. 10, 2001, pp. 12691284.

Edwards, D. P., "Improvements to the correlated–k radiative transfer method: Application to satellite infrared sounding," Journal of Geophysical Research, vol. 105, No. D14, pp. 18, 135–18, 156, Jul. 27, 2000.

Khattatov, Boris V., et al., "Assimilation of satellite observations of long–lived chemical species in global chemistry transport models," Journal of Geophysical Research, vol. 105, No. D23, pp. 29, 135–29, 144, Dec. 16, 2000.

(List continued on next page.)

Primary Examiner—Constantine Hannaher
(74) Attorney, Agent, or Firm—Duft Setter Ollila & Bornsen LLC (57) ABSTRACT

A system for tomographic sounding using infrared radiation, said system comprising a plurality of gas correlation cameras, each of said cameras comprising at least two gas correlation cells, one of said cells filled with a first gas capable of absorbing infrared radiation at one infrared band and another of said cells filled with a second first gas capable of absorbing infrared radiation at another inked band, and a camera with imaging optics for determining both the spectral and energy content of said first infrared band and the spectral and energy content of said second infrared band.

13 Claims, 7 Drawing Sheets-

OTHER PUBLICATIONS

Stephens, G. L., et al., "The Department of Energy's Atmospheric Radiation Measurement (ARM) Unmanned Aerospace Vehicle (UAV) Program," Bulletin of the American Meteorological Society, vol. 81, #12, pp. 2915–2937, Dec. 2000.

Bailak, George V., et al., "MOPITT airborne validation instrument: MOPITT–A," Part of the SPIE Conference on Optical Spectroscopic Techniques and Instrumentation for Atmospheric and Space Research III, Denver, Colorado, Jul. 1999, SPIE vol. 3756.

Edwards, D.P., et al., "Radiative transfer modeling for the EOS Terra satellite Measurement of Pollution in the Troposphere," Journal of Geophysical Research, vol. 104, No. D14, pp. 16,755–16,775, Jul. 27, 1999.

Lamarque, J., et al., "Assimilation of Measurement of Air Pollution from Space (MAPS) CO in a global three–dimensional model," Journal of Geophysical Research, vol. 104, No. D21, pp. 26,209–26,218, Nov. 20, 1999.

Pan, Liwen, et al., "Retrieval of Tropospheric carbon monoxide for the MOPITT experiment," Journal of Geophysical Research, vol. 103, No. D24, pp. 32,277–32,290, Dec. 27, 1998.

Levelt, P. F., et al., Assimilation of MLS ozone measurements in the global three–dimensional chemistry transport model ROSE, Geophysical Research Letters, vol. 25, No. 24, pp. 4493–4496, Dec. 15, 1998.

Smith, Mark, W., et al., The Measurements of Pollutants in the Troposhpere (MOPITT) Airborne Test Radiometer (MATR), The Earth Observer, Jul./Aug. 1998, vol. 10 No. 4, http://eospso.osfc.nasa.gov/eos_observ/7_8_98/p21.html.

Tolton, Boyd, T., et al., "Characterization of the length–modulated radiometer," Applied Optics, vol. 38, No. 28, Aug. 1, 1997, pp. 5409–5420.

Smith, Mark W., "Method and results for optimizing the MOPITT methane bandpass,"0 Applied Optics, vol. 36, No. 18, Jun. 20, 1997, pp. 4285–4291.

Pan, Liwen, et al., "Satellite remote sensing of tropospheric CO and CH4: forward model studies of the MOPITT Instrument," Applied Optics, vol. 34, No. 30, Oct. 20, 1995, pp. 6976–6988.

Andersson, E., et al., "Use of cloud–cleared radiances in three/four–dimensional variational data assimilation," Q.J.R. Meteorol. Soc. 1994, 120, pp. 627–653.

Russell, James M., III et al., "The Halogen Occultation Experiment," Journal of Geophysical Research, vol. 98, No. D6, pp. 10,777–10,797, Jun. 20, 1993.

Grassotti, C., et al., "A Study of Satellite Emission computed Tomography," Advances in Remote Sensing Retrieval Methods, RSRM 1987, Despak Publishing, ISBN 0–937194–13–1, pp. 23–24.

Drummond, J. R., "Novel correlation radiometer: the length–modulated radiometer," Applied Optics, vol. 28, No. 13, Jul. 1, 1989, pp. 2451–2452.

Reichle, Henry G., et al., "Feasibility of determining the vertical profile of carbon monoxide from a space platform," Applied Optics, vol. 28, No. 11, Jun. 1, 1989, pp. 2104–2110.

Lorenc, A. C., "Analysis methods for numerical weather prediction," Quart. J. R. Met. Soc. (1986), 112 pp. 1177–1194.

Fleming, Henry E., "Temperature Retrievals via Satellite Tomography," Advances in Remote Sensing Retrieval Methods, A Despak, 1985, ISBN 0–937194–07–7, pp. 55–69.

Fleming, Henry E., "Satellite Remote Sensing by the Technique of Computed Tomography," Journal of Applied Meteorology, vol. 21, Oct. 1982, pp. 1538–1549.

Smith, W. L., "The Use of Interferometric Radiance Measurements for Sounding the Atmosphere," Journal of the Atmospheric Sciences, vol. 36, Apr. 1979, pp. 566–575.

Ludwig, C. B., "Measurement of Air Pollutants from Satellites. 1: Feasibility Considerations," Applied Optics, vol. 13, No. 6, Jun. 1974, pp. 1494–1509.

Burch, D. E., et al., "Instrument to Monitor CH4, CO, and Co2 in Auto Exhaust," Oct. 1973, Philco–Ford Corp. prepared for Environmental Protection Agency, EPA–650/2–73–030 PB–226 438.

Ellis, P., et al., "Remote sounding of atmospheric temperature from satellites IV. The selective chopper radiometer for Nimbus 5," Proc. R. Soc. Lond. A. 334, Aug. 28, 1973, pp. 149–170.

Taylor, F. W., et al., Radiometer for Remote Sounding of the Upper Atmosphere, Applied Optics, vol. 11, No. 1, Jan. 1972, pp. 135–141.

Houghton, J. T., et al., "Remote sounding of atmospheric temperature from satellites," Proc. Roy. Soc. Lond. A, 320, pp. 23–33 (1970).

Abel, P. G., et al., "Remote sounding of atmospheric temperature from satellites II. The selective chopper radiometer for Nimbus D," Proc. Roy. Soc. Lond. A 320, pp. 35–55 (1970).

Wark, D. O., et al., "Indirect Measurements of Atmospheric Temperature Profiles from Satellites: I. Introduction," Monthly Weather Review, vol. 94, No. 6, Jun. 1966, pp. 351–362.

Kaplan, Lewis D., "Inference of Atmospheric Structure from Remote Radiation Measurements," Journal of the Optical Society of America, vol. 49, No. 10, Oct. 1959, pp. 1004–1007.

King, Jean, "The Radiative Heat Transfer of Planet Earth," Scientific Uses of Earth Satellites, The University of Michigan Press 1958.

Taylor, F. W., Chapter 3 Pressure Modulator Radiometry, Spectrometric Techniques, vol. III 1983 Academic Press, pp. 137–197.

Russell, James M., et al., "Global monitoring of stratospheric halogen compounds from a satellite using gas filter spectroscopy in the solar occultation mode," Applied Optics, vol. 16, No. 3, Mar. 1977, pp. 607–612.

Goers, Uta–Barbara, et al., "A PPLN–OPO–based backscatter absorption gas imaging (BAGI) system as its application to the visualization of fugitive gas emissions," Part of the SPIE Conference on Application of Tunable Diode and Other Infrared Sources for Atmospheric Studies and Industrial Processing Monitoring II. vol. 3758, Jun. 1999, pp. 172–179.

Aniolek, Kenneth W., "Trace gas detection in the mid–IR with a compact PPLN–based cavity ring down spectrometer," SPIE vol. 3758, Jul. 1999, pp. 62–73.

Matr Mopitt Airborne Test Radiometer, retrieved from http://www.eos.ucar.edu/matr/Welcome.html [internet], date of publication unknown, [retrieved on May 30, 2001].

Mopitt, retrieved from: http://www.atmosp. physics.utoronto.ca/Mopitt/home.html [internet], date of publication Oct. 30, 1993, date retrieved May 30, 2001.

"Gas Correlation Spectroscopy" OPTO–Knowledge: The Source for Special Imaging –Press, retrieved from: http://www.techexpo.com/www.opto–knowledge/gas–corr.html, Internet, date of publication, unknown; date retrieved Oct. 3, 2000.

Sandsten, Jonas, Edner, Hans, Svanberg, Sune, and Weibring, Peter, "Gas imaging using gas correlation spectroscopy" retrieved from: http://www–atom.fysik.lth.se/AF-DOCS/Progrep978/c3.htm, Internet, date of publication unknown; date retrieved Oct. 3, 2000.

Smith, Mark W., Technical Report for: Mopitt Airborne Test Radiometer (MATR), retrieved from: http://www.eos.ucar.edu/Matr/Welcome.html, Internet, Date of Publication Mar. 15, 2000, date retrieved unknown.

"Measurements of Pollution in The Troposphere Mopitt," retrieved from: http://www.atmosp.physics.utoronto.ca/Mopitt/home.html, Internet, date of publication unknown, date retrieved Sep. 20, 2000.

Mopitt Project, retrieved from: http://eos.acd.ucar.edu/mopitt, Internet, date of publication Nov. 18, 1999, date retrieved unknown.

Measurements of Pollution in the Troposphere, Mopitt Overview, retrieved from: *http://www.atmosp.physics.utoronto.ca/Mopitt/overview.html* Internet, Date of Publication Aug. 2, 1995; date retrieved Sep. 20, 2000.

Measurement of Pollution in The Troposphere (Mopitt), Measurement of Pollution in The Troposphere (Mopitt) Program; retrieved from *http://www.acd.ucar.edu/as99/Mopitt.html*, Internet, Date of Publication unknown, date retrieved Sep. 20, 2000.

Clerbaux, Cath, Hadji–Lazaro, Juliette. "Assimilation of carbon monoxide measured from satellite in a three–dimensional chemistry–transport model," retrieved from: Journal of Geophysical Research, year of publication 2000. date retrieved unknown.

Baer–Riehart, Jenny, "Erast: Scientific Applications and Technology Commercialization, "Mezzanine Plenary Session, pp. 43–66, Dryden Flight Research Center, Date of Publication unknown, Date retrieved unknown.

Khattatov, Boris, Lyjak, Lawrence, and Gille, John, "On Application of Photochemical Models to the Design of Measurement Strategies," Atmospheric Chemistry Division, National Center for Atmospheric Research; Date of Publication Mar. 2000; pp. 1–4.

Rodgers, Clive D., "Inverse Methods for Atmospheric Sounding Theory and Practice, " Series on Atmospheric, Oceanic and Planetary Physics—vol. 2. World Scientific, Date of Publication 2000.

Smith, Mark W., Remote sensing of atmospheric carbon monoxide with the Mopitt Airborne Test Radiometer (MATR), pp. 1–11 Date of Publication, unknown.

Wyatt, C. L., "Radiometric System Design. Chap. 8 The Radiometric Performance Equation," MacMillan Publishing, pp. 109–113, Date of Publication 1987, New York.

Atmospheric Absorption, Field Measurements of Atmospheric Transmittance, Fig. 5–31, Date of Publication unknown.

Pan, Liwen, et al., "Analysis and Characterization of the Retrieval Algorithm for Measuring Tropospheric CO using the Mopitt instrument," SPIE vol. 2830, pp.159–168, Date of Publication 1996.

Tolton, Boyd T., et al., "Calibration of a length modulated radiometer," SPIE vol. 2830, pp. 253–263. Date of Publication 1996.

* cited by examiner

APPARATUS FOR GAS FILTER CORRELATION RADIOMETRY AND METHODS FOR 2-DIMENSIONAL AND 3-DIMENSIONAL ATMOSPHERIC SOUNDING

RELATED CASES

This application claims the benefit of U.S. provisional application No. 60/255,225 filed Dec. 12, 2000, and U.S. provisional application No. 60/257,675 filed Dec. 20, 2000 and which is hereby incorporated by reference into this application.

BACKGROUND OF THE INVENTION

1. Field of the Invention

This invention relates generally to instruments for measuring atmospheric or related gases by measuring infrared radiation. More particularly, this invention utilizes a plurality of gases that absorb or filter infrared radiation at frequencies (or equivalently at wavelengths) characteristic of each gas; the filtered radiation is passed to an infrared camera with associated electronics and signal processing, which compare the filtered radiation to unfiltered radiation to derive information about the atmospheric or related gases under study.

2. Description of the Prior Art

Gas filter correlation techniques have been used, in particular from spaceborne platforms, to perform atmospheric temperature sounding and to study atmospheric trace gases such as HCl, HF, $CH_4$, and NO in the stratosphere. The gas correlation technique has also been employed from spaceborne platforms to study trace gases, especially CO, in the troposphere. Laser back scatter has been used to image distributions of $CH_4$ and related gases. Infrared cameras have been used extensively to produce images of infrared radiation sources. Fourier transform infrared (FTIR) instruments have been used to measure gas concentrations in the atmosphere remotely. In situ air sampling instrumentation has also been used to measure gas concentrations in the atmosphere.

While infrared cameras produce remotely sensed images of temperature distributions, they mostly measure surface temperatures, with limited information about air temperatures and even less information about gas concentrations. Air sampling instrumentation can measure gas concentrations accurately, but produces very limited information about spatial distributions. FTIR instrumentation can measure a large variety of chemical species simultaneously, but is rarely used in a true imaging system because of the enormously high data rates that result. Gas filter correlation techniques have been combined with imaging systems in the past, but generally with space based scanning imaging systems used only for low spatial resolution measurements. Laser back scatter systems require an active illumination source and are limited to wavelengths that can be produced efficiently by lasers, or by related coherent radiation sources.

Pertinent prior art includes the HALOE, MAPS and MOPITT satellite instruments, and the MATR and MOPITT-A aircraft instruments. MAPS is described by H. G. Reichle, et al., in "Middle and Upper Tropospheric Carbon Monoxide Mixing Ratios as Measured by a Satellite-Borne Remote Sensor During November 1981", J. Geophys. Res., 91, pages 10,865–10,887 (Sep. 20, 1986). MOPITT is described by J. R. Drummond, in "Measurements of Pollution in the Troposphere (MOPITT)", in The Use of EOS for Studies of Atmospheric Physics, pages 77–101, edited by J. C. Gille and G. Visconti, published by North-Holland (1992). MATR is described at http://www.eos.ucar.edu/matr/Welcome html. MOPITT-A is described at http://www.atmosp.physics.toronto.ca.MOPPITT .home.html.

SUMMARY OF THE INVENTION

The subject invention is a gas filter correlation camera and related methods. It is based on a novel combination of two techniques: the use of gas filter correlation radiometry in combination with an infrared camera. The camera comprises a rotatable filter wheel and an infrared camera. The filter wheel is provided with a plurality of chambers, each being filled with a different gas. Each gas corresponds to a gas of interest in the gas volume under study, usually the atmosphere. The camera can be used to produce three dimensional soundings of gas distributions by combining multi-angle viewing with tomographic, or related, reconstruction and retrieval techniques.

Infrared light emitted by the gas volume under study is passed through each of the chambers as the filter wheel rotates, selectively filtering the light in a manner consistent with the infrared radiation absorption characteristics of the various gases. By correlating the position of the filter wheel with the receipt by the infrared camera (and related data-processing equipment) of filtered infrared radiation from the filter wheel, and by analyzing that light for each gas in the filter wheel, the temperature, concentration and other information for each of the corresponding gases in the gas volume under study may be obtained.

One unique aspect of this invention is to combine high spatial resolution images with high specificity to a suite of gases. In principle, any gas that is relatively stable and that has strong infrared absorption features could be imaged. One suite of gases that would be of strong commercial interest is comprised of gases of hydrocarbons, including substituted and unsubstituted saturated and unsaturated hydrocarbons, and particularly including straight-chain compounds like $CH_4$ (methane) and $C_3H_8$ (propane). Another important suite of gases is comprised of CO, $CO_2$, and possibly $O_3$, all of which are important by products of combustion. Another important suite of gases includes species that are emitted by volcanoes, such as HCl, HF, and $SO_2$. Surface temperature and air temperature (possibly using $N_2O$ or possibly using a second $CO_2$ band) would be measured in addition to the gases listed. Several of the gases listed, in particular $CH_4$, $CO_2$, and $N_2O$, are important "greenhouse gases". 3-D volume soundings could be created by means of tomographic reconstruction techniques if the instrument is flown over a given scene using different look angles.

A principal objective of the invention is to produce two dimensional images (and/or three dimensional soundings) of certain geophysical parameters. These include surface temperature, air temperature, and the various suites of gases listed above.

BRIEF DESCRIPTION OF THE DRAWINGS

FIG. 9 illustrates a method of rotating the filter wheel so as to maximize the time that each gas cell is receiving infrared light for passage to the camera receptor.

DETAILED DESCRIPTION OF PREFERRED EMBODIMENTS

This invention, when constructed in a physical embodiment, would have many potential uses. Four of the most important would be detecting emissions of methane (i.e. natural gas) and related hydrocarbons, monitoring and studying wildfires, monitoring and studying air pollution (including greenhouse gases), and monitoring and studying volcanic emissions.

The most likely commercialization of the invention would be for use in detecting emissions of natural gas and other hydrocarbons. The ability to conduct aerial surveys and produce high spatial resolution maps showing the distribution of natural gas (or methane) in the atmosphere above production fields and around storage and transportation facilities would be invaluable in tracking leaks or unintentional releases of this key energy source. Extending the detection capability to related volatile hydrocarbons, such as propane, would open the doors for still more useful applications.

Another likely commercialization of the invention would be for use in monitoring wildfires and providing support for fire fighting efforts. For example, the invention could be used to provide early warning of the location of small, smoldering fires, thus allowing these fires to be quenched before they become full blown problems. For this purpose, the invention could be used to make aerial surveys over high risk areas, using elevated levels of carbon monoxide as a signature for a smoldering fire. This application would require full technical development of the instrument, but probably little development of scientific theory. The invention would probably not even have to provide fully calibrated (or quantitatively accurate) results, but rather provide ready discrimination of levels that are elevated compared to the normal background. Because the instrument uses thermal infrared radiation, it could be used day and night.

For another example, the invention could be used to provide predictive support concerning the probable behavior of wild fires. This application would require extensive development of the underlying scientific theories that predict the behavior of fires, and would most likely require quantitatively accurate results, in order for these results to be incorporated in a useful way in predictive computer models. The underlying assumption is that the quantities measured (namely surface temperature, air temperature, CO and $CO_2$ concentrations) are strongly related to combustion efficiency, and therefore could be useful predictors of the evolution of a fire. The purpose would be to provide information that could be used to direct the efforts of fire fighters for greatest efficiency, and also to provide early warning of possible rapid growth of a fire.

A third possible role for the invention would be for monitoring and studying air pollution, conducted on either a regional basis using an airborne version of the instrument, or on a global basis using a spaceborne instrument Both CO and $CO_2$ are primary combustion by-products produced by industrial sources, by transportation sources, and by fires, both naturally occurring and started by humans. CO, being chemically reactive in the atmosphere, has a great impact on tropospheric oxidation cycles. $CO_2$, as is well known, plays an important role in moderating the thermal environment of the earth and its atmosphere, and hence has a big impact on climate. By using $N_2O$, or a second $CO_2$ band, for temperature sounding, this instrument could potentially provide a relatively simple means of making global measurements of $CO_2$ concentrations.

A fourth role for the invention would be to monitor and study volcanoes. Operating from a fixed site, the instrument could ultimately provide simultaneous images (in real time) of air temperature and concentrations of HCl, HF and $SO_2$ in the plume that issues from a volcanic vent. This could be useful information for predicting imminent eruptions.

The equations that describe radiation transfer in the atmosphere are the basis for calculating atmospheric radiance and its sensitivity to changes in trace gas and temperature fields. These equations can be cast into several different forms. Equation 1 is one straightforward version:

$$I_v(v, zabs) = I_v(v, z_s)\tau(v, z_s, z_{obs}) + \int_{z_s}^{z_{obs}} B(v, T(z))\left[\sum_i k_i(v, z)\rho_i(z)\right]\tau(v, z, z_{obs})dz \quad (1)$$

where $v$=wavenumber, with units of $cm^{-1}$ $I_{84}(v, z_{obs})$=spectral radiance at $v$ at observer altitude $z_{obs}$, with units of $W/(m^2.sr^{-1}.cm^{-1})$ $I_{84}(v, z_s)$=spectral radiance leaving the surface, also with units of $W/(m^2.sr^{-1}.cm^{-1})$ $\tau(v, z_s z_{obs})$=transmittance at $v$ between $z_s$ and $z_{obs}$, which is a dimensionless quantity $B(v, T(z))$=Planck function for temperature T at altitude z, with units of $W/(m^2.sr^{-1}.cm^{-1})$ $k_i(v, z)$=monochromatic absorption coefficient of $i^{th}$ absorber, units $1/(molecules.cm^{-2})$ $\rho_i(z)$=number density of $i^{th}$ absorber at altitude z, with units of molecules. $cm^{-2}$ $\tau(v, z, z_{obs})$=transmittance at wavenumber $v$ from altitude z to the observer at $z_{obs}$ The radiance that is detected by the $n^{th}$ instrument channel is the product of atmospheric spectral radiance and instrument spectral response for that channel, integrated over wavenumber, as shown by Equation 2:

$$I_{n,obs} = \int_{v=-\infty}^{v=+\infty} I_v(v, z_{obs})R_n(v)\,dv \qquad (2)$$

where $I_{n,obs}$=band-integrated radiance observed by $n^{th}$ channel, with units of $W/(m^2 \cdot sr^{-1})$ $I_{84}(v, zobs)$=spectral radiance at wavenumber v at the observer altitude $z_{obs}$(from Eq. 1)

$R_n(v)$=spectral response function of $n^{th}$ instrument channel at wavenumber v The remote sensing process measures electromagnetic radiation, and the profiles of either temperature or trace gases are estimated, or retrieved, based on the amount of electromagnetic radiation that is measured at various wavelengths (multi-spectral approach) or from various angles (multi-angle approach).

The equations that predict radiometric performance for a specific instrument can also be cast into several different forms. The following Equation 3 has been slightly rearranged from forms presented by Wyatt (Wyatt, 1987):

$$SNR = \frac{D*(v)\tau_e\pi\sqrt{A_d/2f}}{4F^2\beta}\int_{v=-\infty}^{v=+\infty} I_v(v, z_{obs})R_n(v)\,dv \qquad (3)$$

where

SNR=signal-to-noise ratio, which is a dimensionless quantity $D^*$=spectral detectivity for a specific detector, with units of cm $Hz^{1/2}$/W v=wavenumber, with units of $cm^{-1}$ $\tau_c$=efficiency of optics, which is a dimensionless quantity $A_d$=area of detector (for a detector which is also the system field stop), with units of $cm^2$ f=frequency bandpass for electronic noise, with units of Hz F=relative aperture, which is a dimensionless quantity $\beta$=chopping factor, which is a dimensionless quantity The remaining terms in the integral are identical to those of Eq. 2. Eqs. 1 and 2 are used to calculate the radiance that is expected for a given scene. Eq. 3 is used to predict the signal-to-noise ratio that is expected for a specific instrument that observes this scene.

Figure 1:
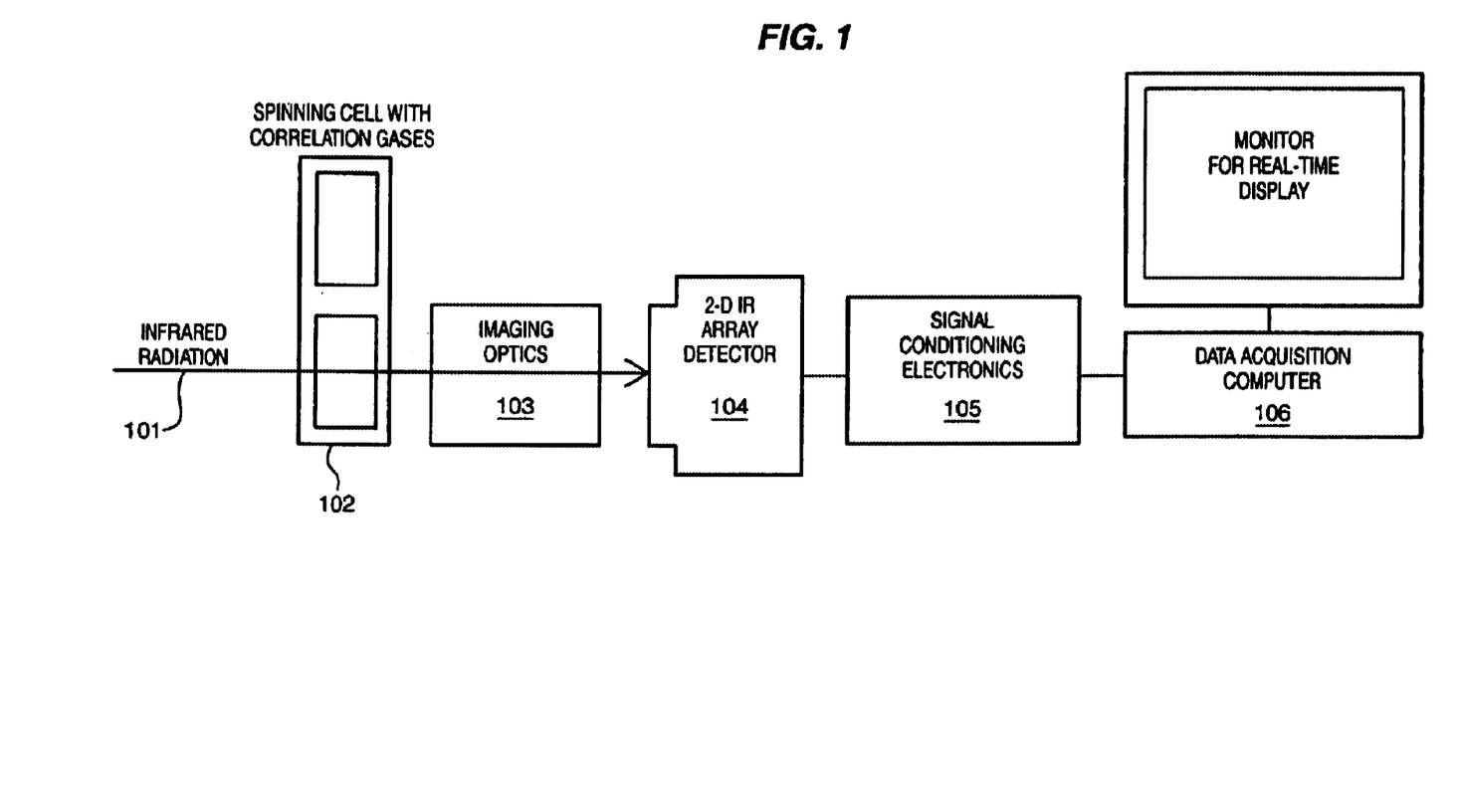
FIG. 1 is a schematic diagram of a first gas correlation camera of the invention.

A representative example of a gas correlation camera of the invention is shown in FIG. 1. Infrared radiation 101 enters respective cells of filter wheel 102. The gas in each cell is different. The gas in each cell absorbs in a characteristic manner a particular band of the infrared radiation spectrum, except for at least one cell that does not absorb infrared radiation. Transmittance plots for gases used in the cells of a gas correlation camera of the invention are set forth in FIG. 3.

Imaging optics 103 produce a desired field of view and correct optical misalignments of the infrared radiation samples as they exit the filter wheel cells. Infrared radiation detector 104 is a 2-D array detector with particular sensitivity to the infrared radiation band under study. Detector 104 receives and detects the infrared radiation emanating from the imaging optics 103. Signal conditioning electronics 105 condition the electrical output of detector 104 before it is received by data acquisition computer 106. The computer compares the infrared radiation sample received from the non-absorbing wheel cell to the infrared radiation samples received from the other wheel cells to determine the spectral profile and energy content of the infrared radiation absorbed by each of the respective gases in the cell. This information permits determination of physical characteristics of the gas volume under study. Data generated by data acquisition computer 106 is displayed on realtime display monitor 107.

The rotating gas wheel 102 is a key element of the correlation camera. Preferred embodiments include two distinct implementations of rotating gas wheel 102. The wheel may be located either in front or inside the optics of infrared camera 104. The advantage of locating wheel 102 in front of infrared camera 104 is simplicity, while the main disadvantage is the fact that wheel 102 must then have its maximum size, as the first lens in a camera is generally the largest optical aperture. Locating the wheel in the midst of the camera optics would be more complicated, but could allow a smaller wheel to be used. This approach is discussed below in connection with FIG. 9.

Figure 2:
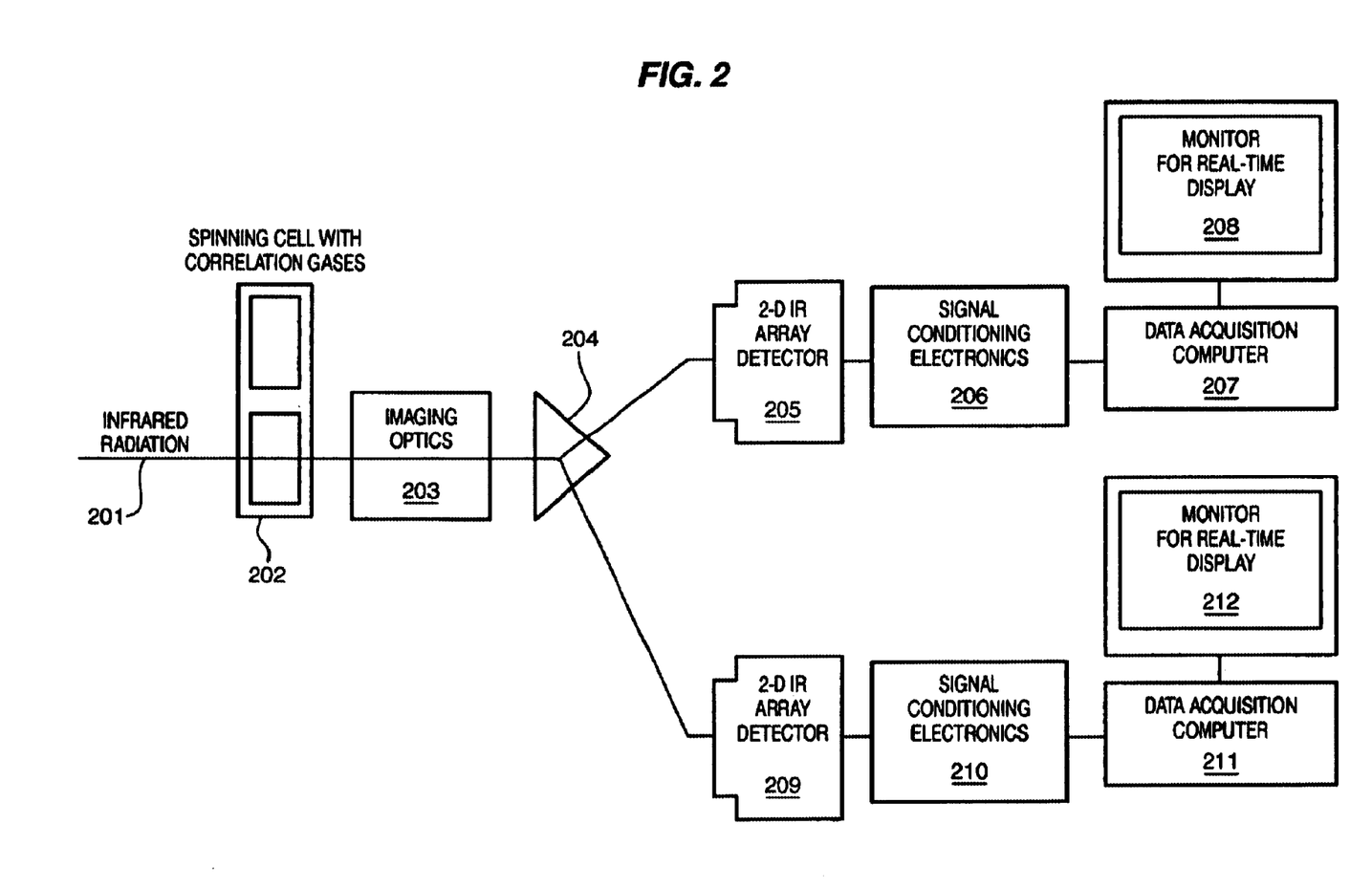
FIG. 2 is a schematic diagram of a second gas correlation camera of the invention.

Another embodiment of a gas correlation camera of the invention is shown in FIG. 2. Filter wheel 202 of this embodiment comprises some chambers containing gases that absorb at one distinct band of the infrared radiation spectrum and other chambers containing gases that absorb at another distinct band of the infrared radiation spectrum, as well as a nonabsorptive cell. A first band could be in a range from about 2000 $cm^{-1}$ to about 2300 $cm^{-1}$ and a second band could be in a range from about 1300 $cm^{-1}$ to about 1360 $cm^{-1}$.

Infrared radiation 201 enters respective cells of filter wheel 202. Imaging optics 203 produce a desired field of view and correct optical misalignments of the infrared radiation samples as they exit the filter wheel cells as the filter wheel 202 rotates to expose each successive cell to the imaging optics 203. Beam splitter 204 splits the infrared radiation data from imaging optics 203 into two beams. One beam enters infrared radiation detector 205, which is an infrared camera with particular sensitivity to the distinct infrared radiation band absorbed by one set of the gases in filter wheel 202. The other beam from beam splitter 204 enters infrared radiation detector 209, which is an infrared camera with particular sensitivity to the distinct infrared radiation band absorbed by the other set of the gases in filter wheel 202. The other components of the system of FIG. 2 performs the same functions in the same way as the corresponding components of FIG. 1.

Infrared radiation detectors 205 and 209 are 2-D array detectors with particular sensitivity to the infrared radiation band under study. They receive and detect the infrared radiation emanating from the imaging optics 203 and beam splitter 204. Signal conditioning electronics 206 and 210 condition the electrical outputs of detectors 205 and 209 before they are received by data acquisition computers 207 and 211. Each computer compares the infrared radiation samples received from the non-absorbing wheel cells to the infrared radiation samples received from the other wheel cells to determine the spectral profile of the infrared radiation absorbed by each of the respective gases in the cell. This information permits determination of the physical characteristics of the gas volume under study. Data generated by data acquisition computers 207 and 211 is displayed on real-time display monitors 208 and 212.

Figure 4:
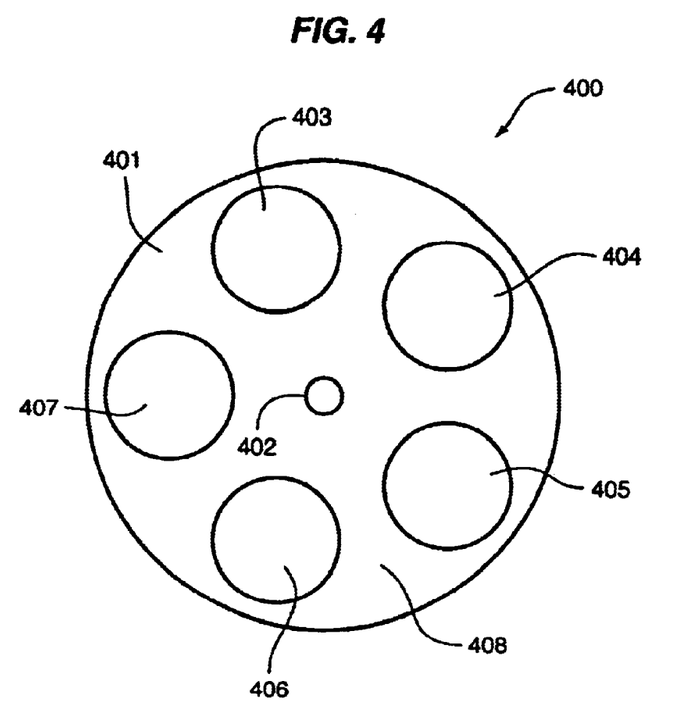
FIG. 4 is a depiction of a first embodiment of a gas correlation filter wheel with multiple gas cells used to filter infrared spectra received by a gas correlation camera of the invention.

A first implementation of a rotating gas wheel is illustrated in FIG. 4. It is a 5-cell wheel 400 that is designed for use over the frequency range from about 2000 $cm^{-1}$ to about 2300 $cm^{-1}$. The body 401 of the cell pivots about axis 402 and contains 5 separate cells: 403, 404, 405, 406 and 407. The gases in each of these cells are as follows:

1. Cell 403=no gas (or optically transparent gas such as $N_2$);
2. Cell 404=$N_2O$;
3. Cell 405=CO;
4. Cell 406=$CO_2$; and
5. Cell 407=band pass interference filter centered on $O_3$ absorption features near 2100 $cm^{-1}$; note that Cell 407 actually does not contain $O_3$ (very reactive) but rather a narrow band pass filter in lieu of $O_3$.

Figure 3:
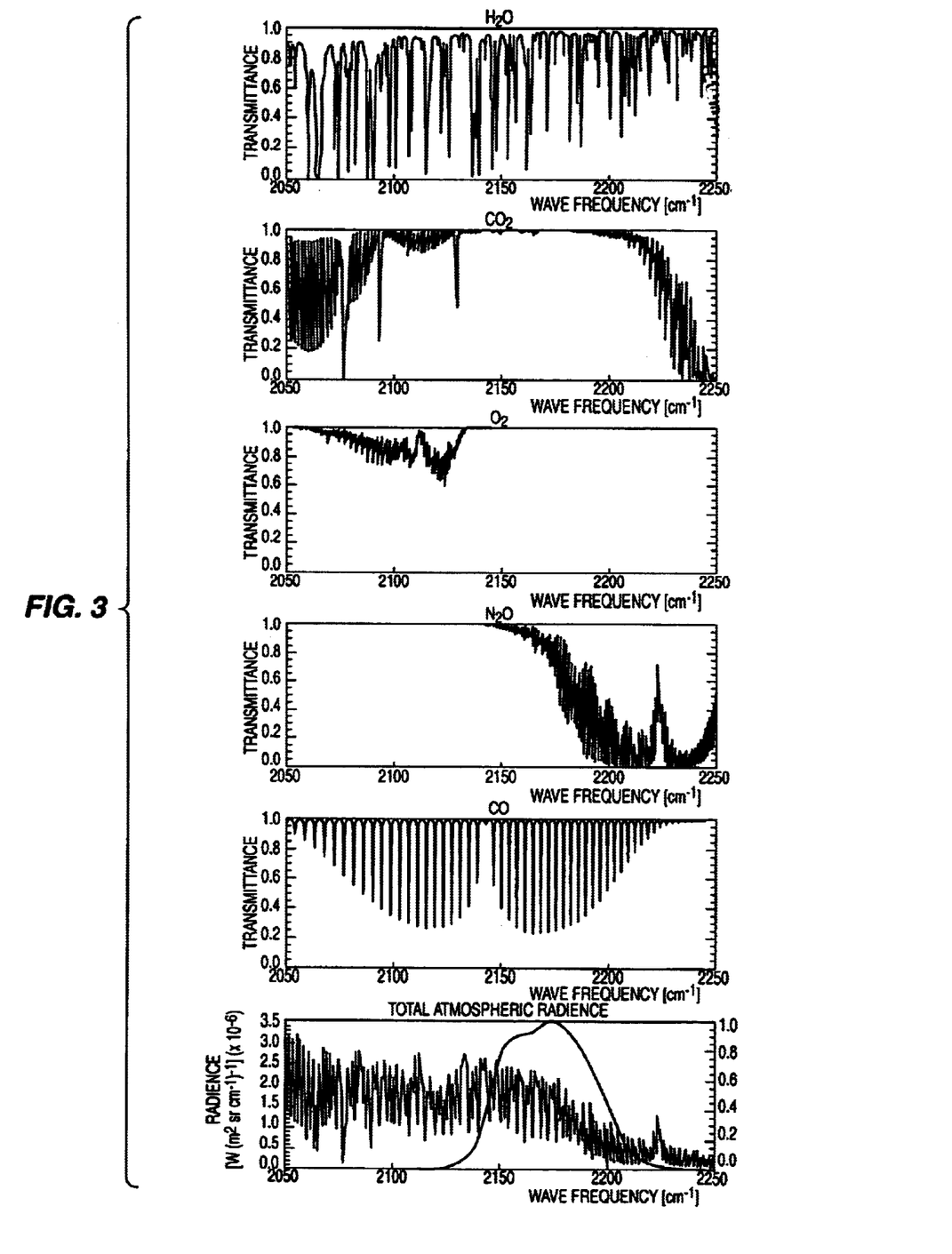
FIG. 3 is a set of transmittance plots for gases used in the cells of a gas correlation camera of the invention.

The gas cells will be separated by opaque, black sectors 408, so that a light interrupter or on/off chopper is an integral part of wheel 400. This wheel is useful for general studies of combustion sources. FIG. 3 illustrates the spectral absorption characteristics of these gases. The information that will be derived from radiometric measurements using each of these cells Is as follows:

1. Cell 403=surface temperature;
2. Cell 404=air temperature;
3. Cell 405=CO amounts;
4. Cell 406=$CO_2$ amounts;
5. Cell 407=$O_3$ amounts.

Figure 5:
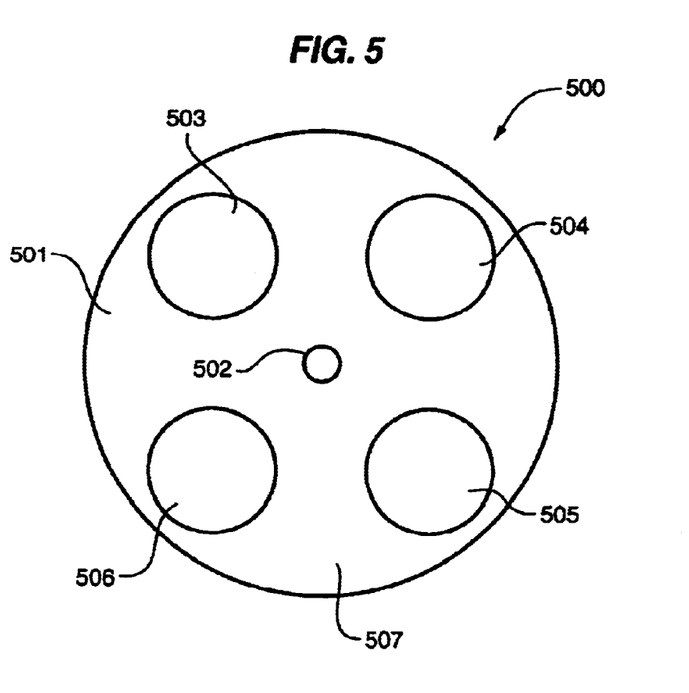
FIG. 5 is a depiction of a second embodiment of a gas correlation filter wheel with multiple gas cells used to filter infrared spectra received by a gas correlation camera of the invention.

A second implementation of a rotating gas cell wheel of the invention is illustrated in FIG. 5. It is a 4-cell wheel 500 for use over a range from about 1300 $cm^{-1}$ to about 1360 $cm^{-1}$. The body 501 of the wheel pivots about axis 502 and contains 4 separate cells: 503, 504, 505, and 506. The gases that will be contained in each of these cells are:

1. Cell 503=no gas (or optically transparent gas such as $N_2$);
2. Cell 504=$CH_4$;
3. Cell 505=$CO_2$;
4. Cell 506=$SO_2$.

The information that will be derived from radiometric measurements using each of these cells is:

1. Cell 503=surface temperature;
2. Cell 504=$CH_4$ amounts or air temperature;
3. Cell 505=$CO_2$ amounts or air temperature; and
4. Cell 506=$SO_2$ amounts.

Again, the gas cells will be separated by opaque, black sectors 507, so that an on/off chopper is an integral part of wheel 500. This wheel will be useful for studies of strong sources Of $SO_2$ In volcanoes. It could also be useful for studying sources of $CH_4$ or $CO_2$. Which of these gases is used to sound for air temperature and which is treated as a species whose concentration is to be measured will depend on the particular application.

Figure 6:
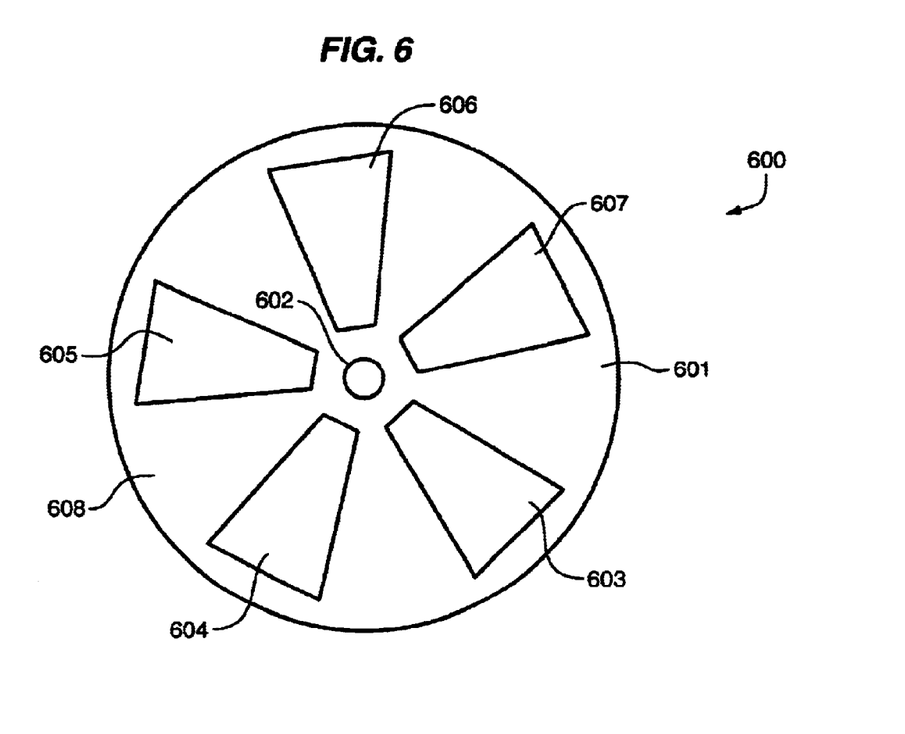
FIG. 6 is a depiction of a third embodiment of a gas correlation filter wheel with multiple gas cells used to filter infrared spectra received by a gas correlation camera of the invention.

A third implementation of a rotating gas cell wheel of the invention is a 5-cell design illustrated in FIG. 6. This wheel 600 has trapezoidal gas cells (603, 604, 605, 606 and 607) rather than the round cells of the wheels of FIGS. 4 and 5. It rotates about pivot 602. The cells may be triangular rather than trapezoidal.

The purpose of this design is to maximize the surface area of the cells on the wheel. This reduces noise and results in cleaner and more reproducible data in analysis of the signals generated by the CCD detector of the infrared camera. Again, the gas cells will be separated by opaque, black sectors 608, so that an on/off chopper is an integral part of wheel 600, although the width of the chopper segments is maximized as much as possible.

The wheel 600 of FIG. 6 can be configured similarly to the wheel 400 of FIG. 4 so as to be useful over the frequency range from about 2000 $cm^{-1}$ to about 2300 $cm^{-1}$. The body 601 of the cell pivots about axis 602. The gases in each of the separate 5 are as follows:

1. Cell 603=no gas (or optically transparent gas such as $N_2$);
2. Cell 604=$N_2O$;
3. Cell 605=CO;
4. Cell 606=$CO_2$; and
5. Cell 607=band pass interference filter centered on $O_3$ absorption features near 2100 $cm^{-1}$.

This wheel is useful for general studies of combustion sources. The information that will be derived from radiometric measurements using each of these cells is as follows:

1. Cell 603=surface temperature;
2. Cell 604=air temperature;
3. Cell 605=CO amounts;
4. Cell 606=$CO_2$ amounts;
5. Cell 607=$O_3$ amounts.

Figure 7:
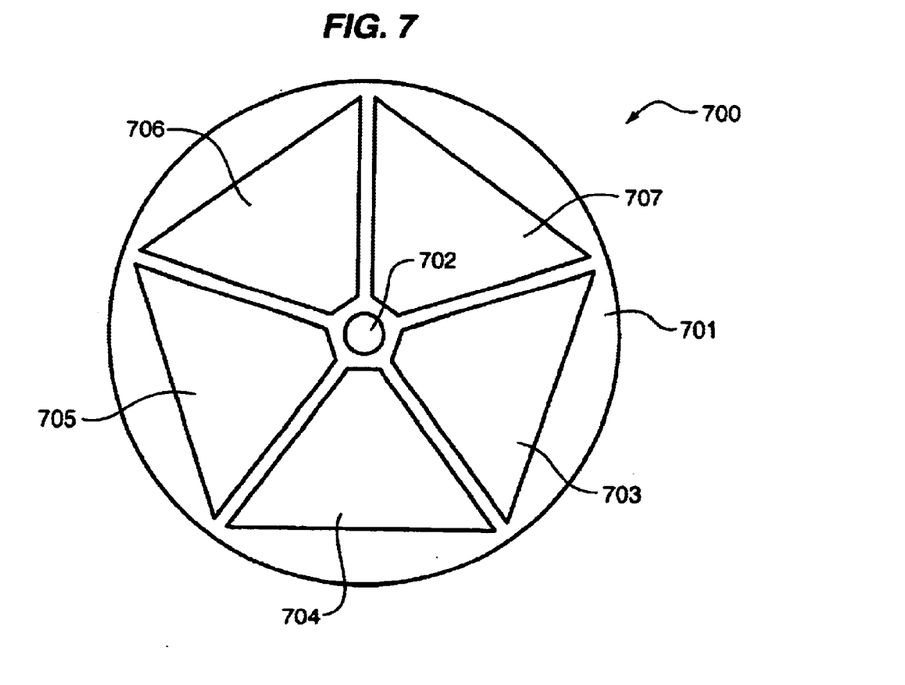
FIG. 7 is a depiction of a fourth embodiment of a gas correlation filter wheel with multiple gas cells used to filter infrared spectra received by a gas correlation camera of the invention.

A fourth implementation of a rotating gas cell wheel of the invention is a 5-cell wheel 700 illustrated in FIG. 7. Here the surface area of the gas cells (703, 704, 705, 706 and 707) has been enlarged to the maximum extent possible without compromising the structural integrity of the wheel itself, which rotates about pivot 702. The chopper spindles 701 have correspondingly been reduced to the maximum extent possible. This wheel is probably not useful for the types of measurements discussed above because the presence of some significant chopper structure is important to making those measure accurately. This wheel would, however, be useful for measuring solar infrared radiation.

Figure 8:
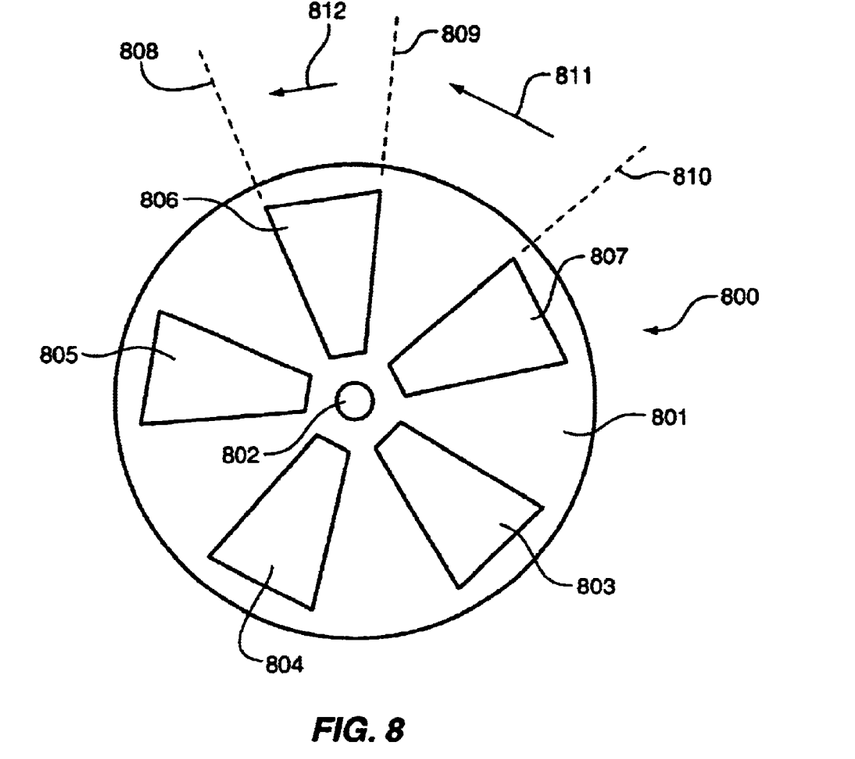
FIG. 8 is a depiction of the gas correlation filter wheel of FIG. 6

FIG. 8 is a depiction of the gas correlation filter wheel 800 of FIG. 6 illustrating a method of rotating the 5-cell filter wheel so as to maximize the time that each gas cell (803, 804, 805, 806 and 807) is receiving infrared light for passage to the infrared camera. The purpose of this method is to increase the efficiency and throughput of the filter wheel and hence the gas correlation camera as whole.

To this end, the wheel rotates, but not at a steady rate. The point is to reduce the time that the imaging optics see the chopper spindles 801 and correspondingly increase the time that the optics see each of the cells. Rotational velocity 811 (shown as a vector between reference lines 809 and 810) is increased when a chopper spindle 801 is blocking the imaging optics. Rotational velocity 812 (shown as a vector between reference lines 808 and 809) decreases when a gas cell is seen by the imaging optics. The net effect is to minimize the time that the imaging electronics spend looking at chopper spindles and maximize the time spent looking at and deriving useful data from gas cells.

Figure 9:
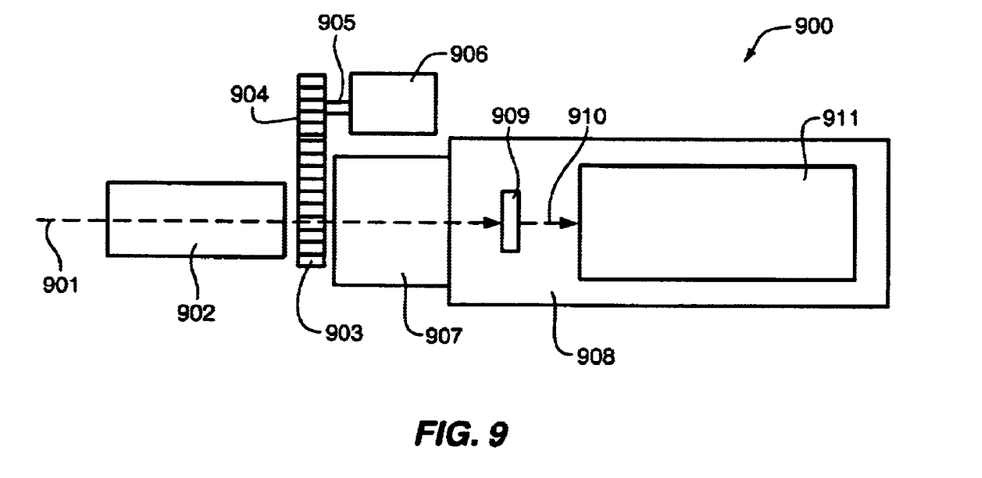
FIG. 9 is a schematic diagram of a third gas correlation camera of the invention.

FIG. 9 is a schematic diagram of a third gas correlation camera of the invention in which a rotating gas wheel is positioned inside the optics of an infrared camera. The advantage of locating the wheel in front of the infrared camera is simplicity, while the main disadvantage is the fact that the wheel must then have its maximum size, as the first lens in a camera is generally the largest optical aperture. Locating the wheel in the midst of the camera optics would be more complicated, but could allow a smaller wheel to be used.

A gas correlation camera 900 locating the wheel in the midst of the camera imaging optics is illustrated in FIG. 9. Imaging optics 902 comprise a part of the overall imaging of the system. Imaging optics 907 complete the imaging optics of the system. Schematic 908 comprises IR detector 909 and conditioning electronics 911.

The key to this design is the location of relatively small gas filter wheel 903 between imaging optics portion 902 and portion 907. As in designs previously discussed, the cells of the wheel are successively positioned in the optical axis of the imaging optics 902 and 907 so as successively to filter incoming raw infrared radiation 901. After filtration, infrared radiation detected by detector 909 and a corresponding electrical signal 910 is passed to signal conditioning electronics 911.

Wheel 903 is fitted with gear teeth on its exterior. These gear teeth correspond to gear teeth on drive gear 904, which is driven by motor 906 through shaft 906. There are many alternative drive mechanisms known to one of skill in the art. For example, drive gear 904 could instead be a pulley for driving wheel 903.

Figure 10:
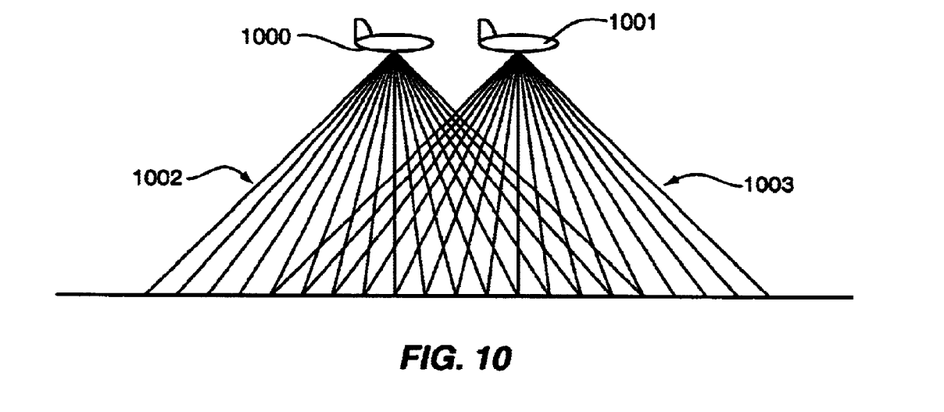
FIG. 10 is a two-dimensional cross sectional view illustrating multi-angle viewing geometry for tomographic sounding using a gas correlation camera of the invention.

FIG. 10 illustrates a system for conducting tomographic sounding using one or more gas correlation cameras of the invention. In this embodiment, the correlation camera(s) are carried either by one or more conventional aircraft or by one or more unmanned aerospace vehicles ("UAVs") 1000 and 1001 and achieve overlapping multi angle views of the atmosphere 1002 and 1003; these views form the basis for 3-D tomographic retrievals. This system will retrieve 3-D distributions of key tropospheric trace gases, as well as air and surface temperature. It also will take advantage of the unique capabilities of aircraft or UAVs as highly programmable and maneuverable observation platforms. While the system of FIG. 10 carries gas correlation cameras, other instrumentation certainly could be carried as part of the payload. Cloud and aerosol remote sensing capabilities would be especially valuable.

While satellites are preferable to aircraft or UAVs for global observations, Aircraft and UAVs possess some unique advantages for high spatial and temporal resolution regional-scale and local-scale observations. An aircraft or UAV can fly in a holding pattern over a given scene to provide continuous temporal coverage of events for as long as the vehicle can remain airborne. The observation time can be extended indefinitely by using a small fleet of UAVs flying in relay fashion. Related to this is the possibility of long signal averaging periods to increase measurement precision. Aircraft and UAVs also offer tremendous flexibility in obtaining the multiple view angles that are required for tomographic sounding of the atmosphere. Finally, the aircraft or UAV flight altitude (up to tens of kilometers) will be much lower than a satellite orbital altitude (hundreds to thousands of kilometers). This will permit much higher spatial resolution in all dimensions.

There are two distinct factors that contribute to the vertical resolution that is attainable with multi-angle remote sounding of the atmosphere. This has been pointed out especially by other workers in the field. One factor is the change in shape, and upwards shift, of the weighting function as the view angle moves off nadir. This effect is actually similar to what occurs in the multispectral approach, as it is related to the rate of change of optical depth as a function of altitude. The second factor is the possibility of applying tomographic retrieval techniques to data that includes multiple views, acquired from multiple angles, of each portion of the atmosphere. For tomographic retrievals, the instrument's field of view, and not just the weighting functions, determines the vertical resolution. Tomographic sounding therefore has the potential to produce vertical resolution superior to that of conventional multi-spectral sounding, for which vertical resolution is limited, even for the hypothetical case of perfectly monochromatic observations, to a couple of kilometers at best and more typically to 8–12 km.

One embodiment of the system of FIG. 10 will use the general Bayesian optimal estimation approach for reconstruction of the 3-D density distributions of atmospheric gases and temperatures from the multi-angle radiance observations. This reconstruction approach is not limited to a particular geometry, number, or type of observations, and it allows calculations of uncertainty of the derived density distributions, thus supplying an important statistical indicator of the quality of final results.

In this technique crude a priori approximations of 3-D density distributions are corrected by observations in regions where observations are available and the calculated uncertainty of the derived distributions decreases accordingly in the corresponding locations. The more observations that are available the more accurate the resulting distributions become, and even in cases where very few observations are available the method still provides approximate estimates of spatial density distributions. The reliability of the estimates can be established from the supplementary uncertainty distributions. The approach can make use of previously (approximately) known properties of distributions of the tropospheric gases under consideration, such as the degree of spatial correlations in both the vertical and horizontal directions. These properties can be approximated from high-resolution chemistry-transport model calculations or from past observations. Particular geometry, number, or type of observations does not limit the practical implementations of the approach. For instance, it is not necessary for the lines-of-sight of the observations shown in FIG. 10 to intersect in space as long as they sample roughly the same volume of interest.

The optimal analysis equations can be presented as Equation 4:

$$x_\alpha = x + K(y - H(x))$$
$$K = B \, H'^T (HB \, H'^T + O)^{-1}$$
$$B_\alpha = (I - KH')B$$

where $x_\alpha$—resulting analyzed 3-D density distributions and temperatures arranged in a vector.

x—αpriori, approximate 3-D density distributions and temperatures arranged in a vector.

y—observations of radiances arranged in a vector.

K—Kalman gain matrix.

$B_\alpha$—error covariance matrix for the analyzed (retrieved) 3-D distributions.

B—error covariance matrix for the a priori distributions.

O—observational error covariance.

H—observational operator, i.e., conversion from gas densities and temperatures in the nodes of a regular grid to the observed radiances. This operator includes both the spatial interpolation and the non-linear forward radiation transfer model.

H'—linearized observational operator, that includes linearized forward radiation transfer model.

During the analysis the a priori distributions x obtained from chemistry-transport models or past observations are used to calculate radiances using the observational geometry and the forward model H. These calculated radiances, H(x), are then compared to the observed radiances y and spatial 3-D distributions $x_\alpha$ of the target chemical species and temperatures are modified to minimize the difference between the calculated (H(x)) and the observed (y) radiances. The resulting field $x_\alpha$ provides the best estimate of the true distribution of the target chemical species and temperatures. Since operator H is non-linear, several iterations of this procedure might be required to reach convergence and the tangent linear model H' and the adjoint tangent linear model $H'^T$ of the utilized radiation transfer model need to be constructed.

The off-diagonal elements of the background error covariance matrix B contain information about characteristic horizontal and vertical correlation scales of the tropospheric gas under consideration. They are usually computed as illustrated in Equation 5:

$$b_{il} = \sqrt{b_j b_i} \exp\left(-\frac{\Delta r_h^2}{2L_h^2}\right) \cdot \exp\left(-\frac{\Delta r_z^2}{2L_z^2}\right)$$

where $L_h$ and $L_z$ are the characteristic correlation scales in the horizontal and vertical directions and $\Delta r_h$ and $\Delta r_z$ are, respectively, horizontal and vertical separations.

A variation of the proposed technique has been applied successfully to the case of the assimilation of TOVS radiance in the ECMWF assimilation package. A similar approach has been applied to reconstructing spatial density distributions of various stratospheric and tropospheric trace gases using observations from satellite-based instruments.

Figure 11:
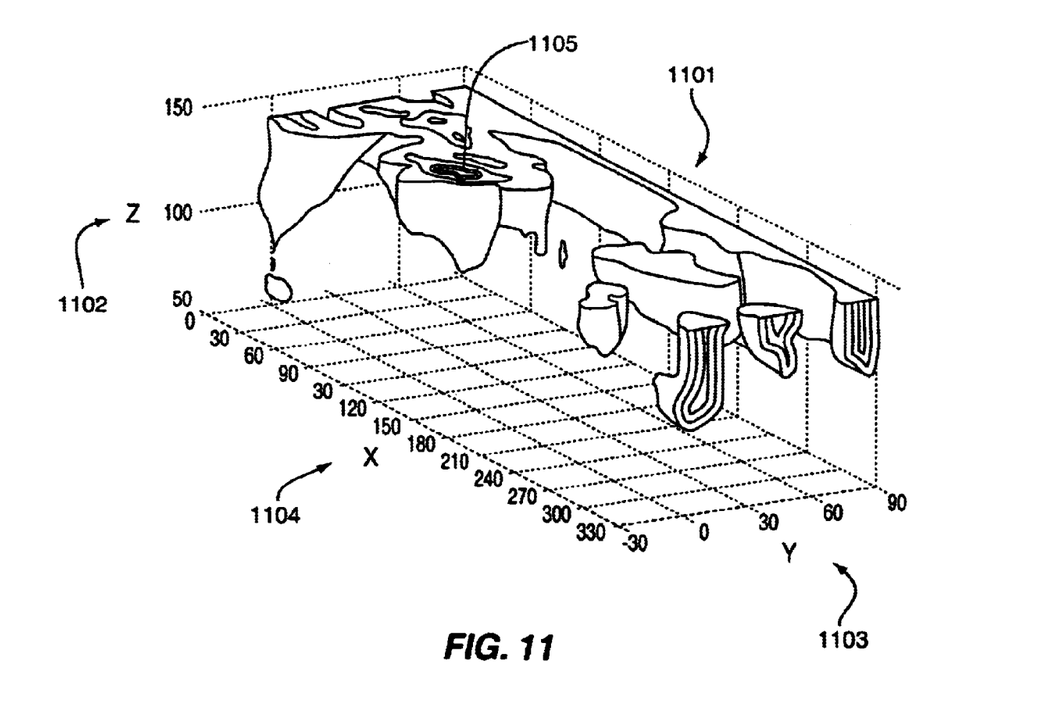
FIG. 11 is an example of the three-dimensional density distribution derived using the tomographic sounding methodology of FIG. 10.

FIG. 11 is a three-dimensional plot of certain data collected by a NASA satellite. The satellite did not use the gas correlation camera of the invention. FIG. 11 is included as a general illustration of a tomographic technique.

Density distribution 1101 is an example of a reconstructed isosurface of instantaneous three-dimensional density distribution of CO in the atmosphere. Density distribution 1101 represents the density of CO gas in the atmosphere sampled in a window by the NASA satellite as it made three circles of the earth. Density distribution 1101 is defined and scaled by Z-axis 1002, Y-axis 1003 and X-axis 1004.

Y-axis 1003 represents the latitudinal position of any given point of the density distribution. X-axis 1104 represents the longitudinal position of any given point of the density distribution 1004. Z-axis 1002 represents the "model level," which corresponds to the position of any given point of the density distribution relative to the surface of the earth. Note that the density distribution has been flipped, so that the highest values on Z-axis 1002 represent points closest to the earth. The shadings on the density distribution plot 1101 represent relative densities, with the highest density 1105 being on the order of 200 ppb.

While the exemplary preferred embodiments of the present invention have been described in detail, those skilled in the art will recognize various changes, modifications, additions, and applications other than those specifically mentioned herein which fall within the spirit of this invention.

What is claimed is:

1. A gas correlation camera comprising at least three gas correlation cells, one of said cells filled with a first gas capable of absorbing infrared radiation at one infrared band, and another of said cells filled with a second gas capable of absorbing infrared radiation at another infrared band, and a third of said cells that does not absorb infrared radiation, and wherein the gas correlation camera further comprises a camera with imaging optics and 2-D array detector for determining the spatial distributions of both the spectral and energy content of said first infrared band and the spectral and energy content of said second infrared band and using the third cell as a null (non-absorbing) energy content reference, and wherein measurements are made using two different absorption bands of $CH_4$, one at wavelengths shorter than 3 micrometers and one at wavelengths greater than 3 micrometers, thus permitting the use of both solar reflected and terrestrially emitted infrared radiation for remote sensing measurements of $CH_4$.

2. The A gas correlation camera comprising at least three gas correlation cells, one of said cells filled with a first gas capable of absorbing infrared radiation at one infrared band, and another of said cells filled with a second gas capable of absorbing infrared radiation at another infrared band, and a third of said cells that does not absorb infrared radiation, and wherein the gas correlation camera further comprises a camera with imaging optics and 2-D array detector for determining the spatial distributions of both the spectral and energy content of said first infrared band and the spectral and energy content of said second infrared band and using the third cell as a null (non-absorbing) energy content reference, and wherein measurements are made using two different absorption bands of $CO_2$, thus permitting the simultaneous retrieval of atmospheric temperature distributions and $CO_2$ distributions.

3. The A system for measuring the spatial distribution of atmospheric infrared radiation from multiple view angles for tomographic sounding with high specificity to the absorption bands of specific atmospheric gases, said system comprising one or more pas correlation cameras, each of said cameras comprising at least three gas correlation cells, one of said cells filled with a first gas capable of absorbing infrared radiation at one infrared band, and another of said cells filled with a second g capable of absorbing infrared radiation at another infrared band, and a third of said cells that does not absorb infrared radiation, said system further comprising a camera with imaging optics for determining the spatial distributions of both the spectral and energy content of said first infrared band and the spectral and energy content of said second infrared band and using the third cell as a null (non-absorbing) energy content reference, an aircraft carrying the said one or more gas correlation cameras, and wherein said gas correlation camera(s) is (are) positioned in said aircraft so as to take multi-angle measurements of infrared radiation passing through the same portion of the atmosphere by making repeated observation passes with different viewing geometries.

4. A system for measuring the spatial distribution of atmospheric infrared radiation from multiple view angles (as required for tomographic sounding) with high specificity to the absorption bands of specific atmospheric gases, said system comprising one or more gas correlation cameras, each of said cameras comprising at least three gas correlation cells, one of said cells filled with a first gas capable of absorbing infrared radiation at one infrared band, and another of said cells filled with a second gas capable of absorbing infrared radiation at another infrared band, and a third of said cells that does not absorb infrared radiation, said system further comprising a camera with imaging optics for determining the spatial distributions of both the spectral and energy content of said first infrared band and the spectral and energy content of said second infrared band and using the third cell as a null (non-absorbing) energy content reference, an aerospace vehicle carrying the said one or more gas correlation cameras, and wherein said gas correlation camera(s) is (are) positioned in said aerospace vehicle so as to take multi-angle measurements of infrared radiation passing through the same portion of the atmosphere by making repeated observation passes with different viewing geometries.

5. A system for measuring the spatial distribution of atmospheric infrared radiation from multiple view angles (as required for tomographic sounding) with high specificity to the absorption bands of specific atmospheric gases, said system comprising one or more gas correlation cameras, each of said cameras comprising at least three gas correlation cells, one of said cells filled with a first gas capable of absorbing infrared radiation at one infrared band, and another of said cells filled with a second gas capable of absorbing infrared radiation at another infrared band, and a third of said cells that does not absorb infrared radiation, said system further comprising a camera with imaging optics for determining the spatial distributions of both the spectral and energy content of said first infrared band and the spectral and energy content of said second infrared band and using the third cell as a null (non-absorbing) energy content reference, an unmanned aerospace vehicle carrying the said one or more gas correlation cameras, and wherein said gas correlation camera(s) is (are) positioned in said unmanned aerospace vehicle so as to take multi-angle measurements of infrared radiation passing through the same portion of the atmosphere by making repeated observation passes with different viewing geometries.

6. A system for measuring the spatial distribution of atmospheric infrared radiation from multiple view angles (as required for tomographic sounding) with high specificity to the absorption bands of specific atmospheric gases, said system comprising one or more gas correlation cameras, each of said cameras comprising at least three gas correlation cells, one of said cells filled with a first gas capable of absorbing infrared radiation at one infrared band, and another of said cells filled with a second gas capable of absorbing infrared radiation at another infrared band, and a third of said cells that does not absorb infrared radiation, said system further comprising a camera with imaging optics for determining the spatial distributions of both the spectral and energy content of said first infrared band and the spectral and energy content of said second infrared band and using the third cell as a null (non-absorbing) energy content reference, two or more aerospace vehicles carrying the said one or more gas correlation cameras, and wherein said gas correlation camera(s) is (are) positioned in said two or more aerospace vehicles so as to take multi-angle measurements of infrared radiation passing through the same portion of the atmosphere by making repeated observation passes with different viewing geometries.

7. A system for tomographic sounding using infrared radiation, said system comprising:
   (a) a plurality of gas correlation cameras, each of said cameras comprising:
      i) at least two gas correlation cells, one of said cells filled with a first gas capable of absorbing infrared radiation at one infrared band and another of said cells filled with a second first gas capable of absorbing infrared radiation at another infrared band;
      ii) a camera with imaging optics for determining both the spectral and energy content of said first infrared band and the spectral and energy content of said second infrared band; and
   (b) a plurality of aerospace vehicles, each carrying one of said plurality of gas correlation cameras.

8. The system of claim 7 wherein at least two of said plurality of gas correlation cameras are positioned in at least two of said plurality of aerospace vehicles so as to take measurements of infrared radiation emanating from the ground.

9. The system of claim 8 wherein said at least two correlation cameras are further positioned to take measurements of infrared radiation emanating at least in part from the same area of ground.

10. The system of claim 7 wherein said aerospace vehicle is an unmanned aerospace vehicle.

11. A system for tomographic sounding using infrared radiation, said system comprising:
   (a) a gas correlation camera comprising;
      i) at least two gas correlation cells, one of said cells filled with a first gas capable of absorbing infrared radiation at one infrared band and another of said cells filled with a second first gas capable of absorbing infrared radiation at another infrared band;
      ii) a camera with imaging optics for determining both the spectral and energy content of said first infrared band and the spectral and energy content of said second infrared band, and
   (b) an aerospace vehicle carrying one of said gas correlation cameras.

12. The system of claim 11 wherein said gas correlation camera is positioned in said aerospace vehicle so as to take repeated measurements of infrared radiation emanating from the same area of ground when said aerospace vehicle makes repeated passes over said same area of ground.

13. The system of claim 11 wherein said aerospace vehicle is an unmanned aerospace vehicle.

* * * * *